United States Patent [19]

Womack

[11] Patent Number: 5,614,224
[45] Date of Patent: Mar. 25, 1997

[54] NUTRITIONAL SUPPLEMENT FOR DIABETICS

[76] Inventor: Rick W. Womack, 9707 Richmond Ave., Suite 50, Houston, Tex. 77042

[21] Appl. No.: 425,582

[22] Filed: Apr. 20, 1995

[51] Int. Cl.$^6$ ............ A61K 31/195; A61K 33/24; A23L 1/30
[52] U.S. Cl. ............ 424/646; 424/655; 426/74; 514/561
[58] Field of Search ............ 424/646, 655; 514/561; 426/74, 656

[56] References Cited

U.S. PATENT DOCUMENTS 5,164,384  11/1992  Paul .................................. 514/188
5,292,538   3/1994  Paul .................................. 426/74

*Primary Examiner*—Phyllis G. Spivack
*Attorney, Agent, or Firm*—Jeffrey L. Streets

[57] ABSTRACT

A daily nutritional supplement and method of administering it to assist in the metabolism of glucose are disclosed. The supplement includes sources of vanadate and chromium as well as L-carnitine.

19 Claims, No Drawings

NUTRITIONAL SUPPLEMENT FOR DIABETICS

FIELD OF THE INVENTION

The present invention relates to nutritional supplements and method of using them which assist in the metabolism of glucose. More particularly, the present invention relates to a nutritional supplement containing ingredients which together perform insulin-like functions to reduce glucose toxicity symptoms and reduce or eliminate the need to administer insulin to people with diabetes. The supplement may be used as a treatment, preventative measure, or cure for poor glucose metabolism or diabetes.

BACKGROUND OF THE DISCLOSURE

Diabetes mellitus is caused in almost all instances by diminished rates of secretion of insulin by the beta cells of the islets of Langerhans in the pancreas. Diabetes is usually divided into two different types: juvenile diabetes that usually, but not always, begins in early life, and maturity-onset diabetes that usually, but not always, begins in later life and mainly in obese persons.

Maturity-onset type of diabetes is likely to occur in those with a family history of diabetes and is characterized by blurred vision, itching, unusual thirst, drowsiness, obesity, fatigue, skin infections, slow healing, and tingling or numbness in the feet. Onset of symptoms is usually later in life. The maturity-onset type of diabetes seems to result from degeneration or suppression of the beta cells as a result of more rapid aging in susceptible persons than in others. Obesity predisposes an individual to this type of diabetes, probably for two different reasons. First, the beta cells of the islets of Langerhans in an obese person become less responsive to stimulation by increased blood glucose levels. Therefore, the surge of insulin secretion following a meal is less marked in obese persons. Second, Obesity also greatly decreases the number of insulin receptors in the insulin target cells throughout the body. For these reasons, increased quantities of insulin are required to have the same metabolic effects in obese persons as in non obese person.

Most of the pathology of diabetes mellitus can be attributed to one of three major effects of insulin lack. First, low levels of insulin cause a decrease in the utilization of glucose by the body cells with a resultant increase in blood glucose concentration to as high as 300 to 1200 mg/dl. Second, insulin lack causes a markedly increased mobilization of fats from the fat storage areas, resulting in abnormal fat metabolism as well as deposition of lipids in vascular walls to cause atherosclerosis. Third, insulin lack can result in a depletion of protein in the tissues of the body.

Typical treatment of diabetes mellitus, including full-blown cases of maturity-onset diabetes, involves administering enough insulin so that the patient will have as nearly normal carbohydrate, fat, and protein metabolism as possible. Optimal therapy can prevent most acute effects of diabetes and greatly delay the chronic effects as well.

Insulin is available in several different forms. Regular insulin has a duration of action lasting from 3 to 8 hours, whereas other forms of insulin are absorbed slowly from the injection site and therefore have effects that last as long as 10 to 48 hours. Ordinarily, the severely diabetic patient is given a single dose of a longer-acting insulin each day to increase overall carbohydrate metabolism throughout the day. Then additional quantities of regular insulin are given at those times of the day when the flood glucose level tends to rise too high, such as at meal times. Thus, each patient is established on an individualized pattern of treatment.

Frequently, following a special diet can control maturity-onset diabetes sufficiently so that insulin is no longer required. It is recommended that an individual with maturity-onset diabetes follow a high-carbohydrate, high-fiber diet to reduce the need for insulin and lower the fat levels in the blood.

An estimated 5.5 million Americans are being treated for diabetes. In addition, studies estimate that there are 5 million adults with undetected maturity-onset diabetes and another 20 million having impaired glucose tolerance that may lead to full-blown diabetes. The National Institutes of Health report that undiagnosed diabetes is the reason behind millions losing their vision. Diabetes is the third leading cause of death in the United States.

There is a need for a composition and method for enhancing glucose metabolism in individuals with maturity-onset diabetes and thereby reduce or prevent the necessity of using insulin. It would be desirable if this composition and method were convenient to administer and cost less than insulin so that it could be easily afforded by individuals with low incomes who have no insurance coverage. It would also be desirable if such a composition could be purchased over the counter, thereby making it more widely available to individuals at high risk of maturity-onset diabetes.

SUMMARY OF THE INVENTION

The present invention provides a daily nutritional supplement for improving glucose metabolism comprising an effective amount of a source of chromium, an effective amount of a source of vanadate, and an effective amount of L-carnitine. A preferred supplement includes an effective amount of vanadyl sulfate as the vanadate source; an effective amount of a source of chromium selected from the group consisting of chromium picolinate, chromium glucose tolerance factor, and mixtures thereof; and either an effective amount of L-carnitine or sufficient amounts of lysine, vitamin B1, vitamin B6, and iron to allow the person to manufacture an effective amount of L-carnitine.

The preferred daily does of these ingredients include between about 20 mg and about 150 mg vanadyl sulfate, between about 150 mcg and about 600 mcg chromium picolinate, and between about 100 mg and about 1,000 mg L-carnitine. It is recommended that the supplement be divided into substantially equal thirds to be taken with meals. The most preferred daily nutritional supplement contains about 60 mg vanadyl sulfate, about 300 mcg chromium picolinate, and about 150 mg L-carnitine.

The present invention also provides a method for enhancing the natural control of blood glucose levels in a person by daily administration of the nutritional supplement. The preferred sources of vanadate and chromium are vanadyl sulfate and chromium picolinate or chromium glucose tolerance factor, respectively. The daily doses are administered in substantially equal portions with three meals throughout the day and can be used in patients to prevent the development of full blown diabetes or, where the person has diabetes, to reduce the amount of insulin required to control blood glucose levels.

DETAILED DESCRIPTION OF THE PREFERRED EMBODIMENT

The present invention provides a nutritional supplement that enhances glucose metabolism. While the supplement may be used by individuals with no apparent symptoms of diabetes, the supplement is ideal for use by individuals with maturity-onset diabetes or juvenile diabetes to prevent, reduce or eliminate the necessity of using insulin. The supplement contains ingredients which work together to enhance the effect of insulin on the regulation of glucose concentration in the blood by facilitating or assisting metabolism of glucose in the cells of the body.

Nutritional supplements according to the present invention are not intended to eliminate the need for an individual to follow a program of appropriate diet and exercise, nor does it eliminate the need for insulin in all cases. Rather, the supplements of the present invention improve glucose metabolism by enhancing the effects of natural or administered levels of insulin and an appropriate diet and exercise program.

It has been discovered that a nutritional supplement containing effective amounts of L-carnitine and metabolically available forms of vanadate and chromium improves metabolism of glucose, particularly in individuals with maturity-onset diabetes. These components perform different insulin-like functions which, when administered in appropriate ratios and forms, enhance the metabolism of glucose in substantially the same way as insulin itself.

As discussed above, insulin performs at least two important functions. First, insulin improves the utilization of glucose by the body cells which in turn controls blood glucose concentrations from getting too high. Second, insulin transports fatty acids to fat cells for storage, thereby reducing the mobilization of fats from fat storage areas which can result in abnormal fat metabolism as well as deposition of lipids in vascular walls to cause atherosclerosis.

The first function of insulin mentioned above, that of improving the utilization of glucose, is enhanced by the combination of vanadate and chromium. Vanadate ions, like insulin, stimulate glucose transport, activate glycogen synthase, increase glycogen syntheses in fat cells, and stimulate carbohydrate uptake in the liver. Glycogen synthase is an enzyme which causes the conversion of glucose into glycogen. Glycogen itself is a polysaccharide which is the chief carbohydrate storage material in humans. It has been found that maximum glycogen synthase activation produced by vanadate is indistinguishable from that of insulin. Evidence that strongly suggests a common mechanism of action for insulin and vanadate includes the following findings: with maximum insulin, additional quantities of vanadate are without effect; with sub maximal insulin, additional quantities of vanadate increase both the glycogen synthase activation state and 2-deoxyglucose transport to the level obtained with maximum insulin; insulin and vanadate counteract the activating effect of adrenaline on glycogen phosphorylase in a similar manner; adrenaline partially reverses vanadate and insulin activated glycogen synthase in a similar manner; and vanadate and insulin activate glycogen synthase within similar time frames. Thus, the presence of in-vivo vanadate can lead to improved glucose metabolism and enhance the effects of natural or administered levels of insulin. The preferred source of vanadate is vanadyl sulfate. Once ingested, vanadyl sulfate typically forms vanadate which is a salt of vanadic acid. While doses as low as 10 mg of vanadyl may provide some enhancement of glucose metabolism, the preferred dosage of vanadyl sulfate for an individual with diabetes weighing from about 150 pounds to about 250 pounds is in the range between about 30 mg and 150 mg per day. The most preferred dosage of vanadyl sulfate is about 60 mg per day. Whereas vanadyl sulfate has been previously included in certain dietary supplements, dosages ranging between 1 mcg and 1,000 mcg (1 mg) are inadequate to provide significant insulin-like effects.

Chromium, like vanadyl sulfate, possesses properties which both mimic and enhance the effects of insulin. Chromium enhances the effects of insulin by indirectly assisting amino acid uptake by muscle, stimulates protein synthesis and retards the rate of protein breakdown. Many clinical studies with supplemental chromium have shown only modest improvements in glucose tolerance due to poor absorption of nutritional (trivalent) chromium. In this respect, trivalent chromium has a strongly positive charge that impedes its movement across cell membranes. Due to the presence of competing ions such as copper, iron, manganese and zinc in the human body, adequate absorption of chromium occurs only when the metal is associated with the natural chelating agent, picolinic acid. Because of its unique structure, picolinic acid has a strong affinity for transitional metals such as zinc, manganese, and chromium. In this respect, it binds tightly to these metals thereby neutralizing their positive charges and expediting their movement across cell membranes.

It is preferred that chromium be provide in a biologically active form of chromium, particularly chromium picolinate or chromium glucose tolerance factor. In chromium picolinate, the picolinic acid serves as an effective metal chelator that improves the utilization and uptake of the chromium and plays an important physiological role in trace mineral absorption. Chromium is believed to be the active factor while the picolinic acid serves as the chelator to improve bioavailability. Animal studies have shown chromium picolinate to be absorbed and retained five to ten times better than other forms of chromium and have also found it to be remarkably safe. The preferred dosage of chromium picolinate for an individual with diabetes weighing from about 150 pounds to about 250 pounds is in the range between about 150 mcg and about 600 mcg per day, with about 300 mcg per day being most preferred. The preferred dosage of chromium glucose tolerance factor is between about 50 mcg and about 400 mcg per day, with about 100 mcg per day being most preferred. While the supplement may include only one form of chromium, it is preferred that the supplement include both forms in their preferred doses given above.

The second function of insulin mentioned above, that of transporting fatty acids to fat cells for storage, is enhanced by L-carnitine. By preventing fatty build-up, this amino acid aids in weight loss, decreases the risk of heart disease, and improves athletic ability. Carnitine can be manufactured in the body if sufficient amounts of lysine, B1, B6 and iron are available. However, vegetarians are more likely to be deficient in carnitine due to a diet that is low in lysine. The preferred dosage of L-carnitine for an individual with diabetes weighing from about 150 to about 250 pounds is in the range between about 100 mg and about 1,000 mg per day. The most preferred dosage of L-carnitine is about 150 mg.

Because L-carnitine can be manufactured in the body, it is possible to complement the L-carnitine with sufficient amounts of lysine, vitamin B1, vitamin B6 and iron to facilitate production of L-carnitine. Therefore, while lysine, vitamin B1, vitamin B6 and iron are not essential to the function of the present invention, it is preferred that the supplement include between about 5 and about 10 mg per day of both vitamins B1 and B6, and between about 10 mg and about 25 mg of iron. It is most preferred that vitamins B1 and B6 be supplied by a dose of between about 30 mg and about 70 mg of a B-complex.

The present invention combines vanadyl sulfate, chromium picolinate and L-carnitine in a nutritional supplement to produce insulin-like effects that prevent, reduce or eliminate the need to administer insulin. It is preferred that the supplement be taken throughout the day to be available to the cells as needed. It is particularly preferred that the daily dosage be taken in approximately equal amounts with breakfast, lunch and dinner. This method supplies the nutrients to assist in glucose metabolism following mealtime when they are needed the most.

It may be desirable that the nutritional supplement include other certain vitamins, minerals, amino acids, enzymes and/or herbs. These additional ingredients may be included in a single pill along with the vanadyl sulfate, chromium picolinate and L-carnitine or may be taken as a separate pill taken more or less simultaneously.

Vitamins that are particularly beneficial to the metabolism of glucose are the B-complex vitamins and vitamin A. Even where the supplement includes L-carnitine, it is preferred that the supplement include between about 5 and about 10 mg per day of both vitamins B1 and B6, and between about 40 mg and about 60 mg per day of niacinamide (vitamin B3). It is most preferred that the supplement include a dose of between about 30 mg and about 70 mg per day of B-complex vitamins where the amounts of vitamins B1, B3 and B6 included therein are about 6 mg, 50 mg and 6 mg, respectively.

Vitamin A is necessary to the utilization of protein. It may be taken as beta-carotene, which is converted to vitamin A in the liver, or as the vitamin itself. The preferred dose of vitamin A is between about 10,000 IU and about 20,000 IU per day, with the most preferred being about 15,000 IU per day.

Minerals are also important in the metabolism of glucose and may be ingested from food or included in a supplement. In order to be certain that sufficient amounts of the most important minerals are available, it is preferred that the supplement also include magnesium, potassium, calcium, copper, selenium, and zinc. The preferred daily doses of these minerals is about 380 mg magnesium, about 114 mg potassium, about 760 mg calcium, about 2 mg copper, about 80 mcg selenium, and about 50 mg zinc. It should be recognized that the amounts of these minerals can vary widely within the scope of the present invention.

L-glutamine is an important amino acid in curbing fatigue and the craving for sugar. The preferred dose of L-glutamine is between about 100 mg and about 500 mg per day, with about 300 mg per day being most preferred.

Many different enzymes may be incorporated into the supplement, in accordance with the invention, to assist in the digestion of food. The preferred enzymes include pancreatin, amylase, papain, lipase and betaine.

Pancreatin is an enzyme derived from the secretions of an animal pancreas. It is preferred that the supplement include pancreatin in doses ranging between about 50 and about 150 mg per day. It is most preferred that the supplement include about 100 mg pancreatin per day.

Amylase is an effective digestive enzyme secreted in high concentrations in the human body. Amylase is found in saliva and works to breaks down carbohydrates. It is preferred that the supplement include amylase in doses ranging between about 50 and about 150 mg per day. It is most preferred that the supplement include about 100 mg amylase per day.

Papain is a proteolytic enzyme that works exclusively to break down proteins. It is preferred that the supplement include papain in doses ranging between about 25 mg and about 70 mg per day each. It is most preferred that the supplement include about 45 mg per day of papain.

Lipase is an enzyme that aids in the digestion of fat. It is preferred that the supplement include lipase in doses ranging between about 80 mg and about 230 mg per day each. It is most preferred that the supplement include about 150 mg lipase per day.

Betaine, a preferred form of hydrochloric acid (HCl), aids in the digestion of tough foods, such as fibrous meats, vegetables, and poultry. It is also preferred that the supplement include between about 100 mg and 200 mg per day of betaine, with about 150 mg per day being most preferred.

Herbs beneficial against the causes or symptoms of diabetes, including high blood pressure, may also be incorporated into the supplement without departing from the scope of the invention. These herbs include, but are not limited to, ginseng, huckleberry, evening primrose oil, garlic, gotu kola, juniper berries, and suma. The preferred herbs are ginseng and huckleberry. The preferred dose of ginseng is between about 150 mg and about 350 mg per day, with about 275 mg per day being most preferred. The preferred dose of huckleberry is between about 100 mg and about 200 mg per day, with about 150 mg per day being most preferred.

Guar gum is a water soluble fiber that has been shown to lower blood glucose levels, aid in lowering cholesterol levels, and curb the appetite. Guar gum must be taken as a liquid as should not be included in any pills, capsules, tablets, or other solid forms. However, the nutritional supplement of the present invention could be prepared in the form of a liquid drink which could include guar gum.

The supplement of the present invention can be manufactured in accordance with procedures known in the art. While the supplement may be formed into a pill with starch or a liquid drink, it is generally preferred that the supplement be prepared in a capsule.

EXAMPLE 1

A nutritional supplement was prepared according to the following daily dosages:

| | |
|---|---|
| Vanadyl Sulfate | 60 mg |
| Chromium (Picolinate) | 300 mcg |
| Chromium (Glucose Tolerance Factor) | 100 mcg |
| L-Carnitine | 150 mg |
| L-Glutamine | 300 mg |
| Magnesium | 380 mg |
| Potassium | 114 mg |
| Calcium | 760 mg |
| Copper | 2 mg |
| Vitamin A | 15,000 IU |
| Niacinamide (B-3) | 50 mg |
| Vitamin (B-1) | 6 mg |
| Vitamin (B-6) | 6 mg |
| Selenium | 80 mcg |
| Zinc | 50 mg |
| Pancreatin | 100 mg |
| Papain | 75 mg |
| Amylase | 100 mg |
| Betaine (HCL) | 75 mg |
| Lipase | 150 mg |
| Huckleberry | 150 mg |
| Ginseng | 275 mg |

This daily dosage is divided into six (6) capsules. Two of these six capsules are to be taken along with breakfast, lunch and dinner each day.

While much of the foregoing disclosure has focused on insulin lack, diabetes can also occur in individuals whose pancreas is producing plenty of insulin but the cells of the body are insulin resistant. Vanadyl sulfate can increase the response that a cell has to insulin by activating the insulin receptor sites on the surface of the cell and within the cell. Furthermore, this activation of insulin receptors may be permanent.

The nutritional supplement of the present invention may be used not only as a treatment for poor glucose metabolism or diabetes, but also for prevention of diabetes by giving the metabolism a boost before full-blown diabetes develops. In fact, because the activation of insulin receptors and other effects may be permanent, the supplement could be considered to be a cure for diabetes in some individuals and circumstances.

It will be understood that certain combinations and subcombinations of the invention are of utility and may be employed without reference to other features in subcombinations. This is contemplated by and is within the scope of the present invention. As many possible embodiments may be made of this invention without departing from the spirit and scope thereof, it is to be understood that all matters hereinabove set forth or shown in the accompanying drawing are to be interpreted as illustrative and not in a limiting sense.

While the foregoing is directed to the preferred embodiment, the scope thereof is determined by the claims which follow:

I claim:

1. A daily nutritional supplement for improving glucose metabolism in diabetics comprising:
   an effective amount of a source of chromium;
   an effective amount of a source of vanadate; and
   an effective amount of L-carnitine.

2. The daily nutritional supplement of claim 1 wherein the source of vanadate is vanadyl sulfate.

3. The daily nutritional supplement of claim 2 wherein the amount of vanadyl sulfate is between about 20 mg and about 150 mg.

4. The daily nutritional supplement of claim 3 wherein the source of chromium is selected from the group consisting of chromium picolinate, chromium glucose tolerance factor, and mixtures thereof.

5. The daily nutritional supplement of claim 4 wherein the source of chromium comprises between about 150 mcg and about 600 mcg chromium picolinate and between about 50 mcg and about 400 mcg chromium glucose tolerance factor.

6. The daily nutritional supplement of claim 5 wherein the amount of L-carnitine is between about 100 mg and about 1,000 mg.

7. The daily nutritional supplement of claim 6 wherein the vanadyl sulfate, chromium picolinate and L-carnitine are divided into substantially equal thirds to be taken with meals.

8. The daily nutritional supplement of claim 7 wherein the amount of vanadyl sulfate is about 60 mg.

9. The daily nutritional supplement of claim 8 wherein the amount of chromium picolinate is about 300 mcg, the amount of chromium glucose tolerance factor is about 100 mcg, and the amount of L-carnitine is about 150 mg.

10. A method for enhancing the natural control of blood glucose levels in a person comprising the step of:
    administering a nutritional supplement comprising effective amounts of a source of chromium, a source of vanadate, and L-carnitine.

11. The method of claim 10 wherein the source of vanadate is vanadyl sulfate.

12. The method of claim 11 wherein the source of chromium is selected from the group consisting of chromium picolinate, chromium glucose tolerance factor, and mixtures thereof.

13. The method of claim 12 wherein the source of chromium is chromium picolinate.

14. The method of claim 13 wherein the daily dose of chromium picolinate ranges between about 150 mcg and about 600 mcg per day;
    wherein the daily dose of vanadyl sulfate ranges between about 20 mg and about 150 mg per day; and
    wherein the daily dose of L-carnitine ranges between about 100 mg and about 1,000 mg per day.

15. The method of claim 14 wherein the administered dose of vanadyl sulfate is about 60 mg per day.

16. The method of claim 15 wherein the source of chromium further comprises a daily dose of between about 50 mcg and about 400 mcg chromium glucose tolerance factor.

17. The method of claim 16 wherein the daily doses are administered in substantially equal portions with three meals throughout the day.

18. The method of claim 10 wherein the person has diabetes, and wherein the supplement is administered to reduce the amount of insulin required to control blood glucose levels.

19. The method of claim 17 further comprising the step of:
    continuing to administer the supplement for a period of between about five weeks and about one year.

* * * * *